(12) United States Patent
Dede et al.

(10) Patent No.: US 12,167,906 B2
(45) Date of Patent: Dec. 17, 2024

(54) EMOTION-AWARE SMART REFRIGERATOR

(71) Applicant: TOYOTA MOTOR ENGINEERING & MANUFACTURING NORTH AMERICA, INC., Plano, TX (US)

(72) Inventors: Ercan M. Dede, Ann Arbor, MI (US); Muhamed K. Farooq, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 1017 days.

(21) Appl. No.: 17/143,937

(22) Filed: Jan. 7, 2021

(65) Prior Publication Data

US 2022/0211278 A1    Jul. 7, 2022

(51) Int. Cl.
| | | |
|---|---|---|
| *G06F 3/01* | (2006.01) |
| *A61B 5/00* | (2006.01) |
| *A61B 5/0205* | (2006.01) |
| *A61B 5/11* | (2006.01) |
| *A61B 5/16* | (2006.01) |
| *A61B 5/378* | (2021.01) |

(Continued)

(52) U.S. Cl.
CPC .......... *A61B 5/0205* (2013.01); *A61B 5/0006* (2013.01); *A61B 5/11* (2013.01); *A61B 5/165* (2013.01); *A61B 5/378* (2021.01); *A61B 5/486* (2013.01); *A61B 5/6887* (2013.01); *F25D 29/00* (2013.01); *G06F 3/011* (2013.01); *G06F 3/015* (2013.01); *A61B 5/024* (2013.01); *F25D 2700/04* (2013.01); *F25D 2700/06* (2013.01)

(58) Field of Classification Search
CPC ....... A61B 5/0205; A61B 5/0006; A61B 5/11; A61B 5/165; A61B 5/378; A61B 5/486; A61B 5/6887; A61B 5/024; A61B 8/02; F25D 29/00; F25D 2700/04; F25D 2700/06; G06F 3/011; G06F 3/015
See application file for complete search history.

(56) References Cited

U.S. PATENT DOCUMENTS

| | | |
|---|---|---|
| 9,953,542 B2 | 4/2018 | Mayou |
| 10,365,716 B2 | 7/2019 | Aimone |
| 10,375,033 B2 | 8/2019 | Nagarajan |

(Continued)

FOREIGN PATENT DOCUMENTS

| | | |
|---|---|---|
| CN | 105117450 A  * | 12/2015 |
| CN | 105117450 A1 | 12/2015 |

(Continued)

*Primary Examiner* — KC Chen
(74) *Attorney, Agent, or Firm* — SHEPPARD, MULLIN, RICHTER & HAMPTON LLP; Daniel N. Yannuzzi

(57) ABSTRACT

An emotion-aware smart refrigerator is provided which may include various sensors and presentation mechanisms to identify a user's interest in item(s) contained within the emotion-aware smart refrigerator via an evoked physiological response, such as a visual evoked potential (VEP). The user's level of interest may also be gauged by the emotion-aware smart refrigerator. With consideration given to the user's VEP as well as the user's level of interest, and other considerations such as the user's diet, desired health goals, dietary restrictions, etc., the emotion-aware smart refrigerator may present suggested items and item amounts to the user.

20 Claims, 7 Drawing Sheets

(51) Int. Cl.
*F25D 29/00* (2006.01)
*A61B 5/024* (2006.01)

(56) References Cited

U.S. PATENT DOCUMENTS

| | | | |
|---|---|---|---|
| 2015/0281784 A1* | 10/2015 | Laksono | H04N 21/44008 |
| | | | 725/10 |
| 2015/0313496 A1 | 11/2015 | Connor | |
| 2018/0008145 A1* | 1/2018 | Freer | A61B 5/0006 |
| 2019/0340674 A1* | 11/2019 | Vaananen | F25D 27/005 |
| 2019/0368805 A1 | 12/2019 | Lim | |
| 2020/0012346 A1* | 1/2020 | Schiff | A61B 5/383 |
| 2020/0134291 A1* | 4/2020 | Kim | F25D 11/00 |
| 2022/0282910 A1* | 9/2022 | Jeong | G06N 20/00 |

FOREIGN PATENT DOCUMENTS

| | | |
|---|---|---|
| KR | 20160003211 | 1/2016 |
| KR | 20160044387 A | 4/2016 |
| WO | 2018177313 A1 | 10/2018 |
| WO | 2019129248 A1 | 7/2019 |

* cited by examiner

EMOTION-AWARE SMART REFRIGERATOR

TECHNICAL FIELD

The present disclosure relates generally to smart refrigerators.

DESCRIPTION OF RELATED ART

A refrigerator can refer to an appliance that supplies cold air generated by an evaporator to a storage compartment to maintain and store the freshness of various foods (or other items) for some period of time. Typically, the storage compartment of a refrigerator can be divided into multiple compartments. A first compartment may be a refrigeration compartment (the temperature of which may be variable, but is typically maintained at approximately 3° C. to refrigerate food or other items). A second compartment may be a freezer compartment (the temperature of which, again, may be variable, but can be maintained at approximately −20° C. to freeze food or other items).

To cool the refrigeration and freezer compartments, a cooling cycle can be repeated in which a refrigerant can be compressed, condensed, expanded, and made to evaporate using certain components. Those components may include a compressor, a condenser, an expander, and an evaporator. In some refrigerators, a single evaporator component may operate to cool both the refrigeration and freezer compartments. In some refrigerators, each of the refrigeration and freezer compartments may be cooled by a separate evaporator.

BRIEF SUMMARY OF THE DISCLOSURE

In accordance with one embodiment, a method may comprise detecting presence of a user proximate to a refrigerator, and presenting visual stimuli prompting a first physiological) response from the user regarding one or more items contained in the refrigerator. The method may further comprise detecting and analyzing the user's first physiological response regarding at least one of the one or more items, and measuring a second physiological response of the user. Further still, the method may comprise presenting targeted information regarding the at least one of the one or more items based on the first and second physiological responses.

In some embodiments, presenting the visual stimuli comprises presenting images representative of the one or more items to the user on a display, and wherein the present images oscillate at unique frequencies.

In some embodiments, presenting the visual stimuli comprises presenting images representative of the one or more items to the user on a display in accordance with a particular order.

In some embodiments, the one or more items correspond to a current inventory of items contained in the refrigerator.

In some embodiments, detecting the user's first physiological response comprises sensing the user's brainwave activity via at least one contactless brainwave sensor configured to wirelessly monitor the user's brainwave activity, the first physiological response comprising a visual evoked potential (VEP) response.

In some embodiments, analyzing the user's VEP response comprises correlating the user's brainwave activity to identify the at least one of the one or more items indicative of an item of interest to the user.

In some embodiments, measuring the second physiological response of the user comprises determining heart rate activity of the user.

In some embodiments, measuring the second physiological response of the user comprises determining at least one of body movements and facial expressions.

In some embodiments, presenting the targeted information comprises presenting a recommended amount of the at least one of one or more items to the user.

In some embodiments, presenting the targeted information comprises assessing at least one of an amount of the at least one of the one or more items and an alternative item to the at least one of the one or more items based on at least one of a user profile, one or more learned characteristics of the user, one or more preferences indicated by the user, a day, and a time of day.

In accordance with another embodiment, a refrigerator may comprise a presence sensor detecting presence of a user proximate to the refrigerator. The refrigerator may further comprise a visual stimulation generation component to present visual stimuli on a display of the refrigerator prompting a visual evoked potential (VEP) response from the user regarding one or more items contained in the refrigerator. Further still, the refrigerator may comprise a contactless brainwave sensor to detect and analyze the user's VEP response regarding at least one of the one or more items, and an ultrasonic transducer to measure an interest level response of the user. The visual stimulation generation component may further present targeted information regarding the at least one of the one or more items based on the VEP response and the measured interest level response.

In some embodiments, the visual stimulation generation component presents the visual stimuli by presenting images representative of the one or more items to the user on a display, and wherein the present images oscillate at unique frequencies.

In some embodiments, the refrigerator may further comprise an inventory tracking component tracking and maintaining a current inventory of items contained in the refrigerator.

In some embodiments, the refrigerator further comprises a processor to correlate the user's brainwave activity evidenced by the user's VEP response to identify the at least one of the one or more items indicative of an item of interest to the user.

In some embodiments, to measure the physiological response of the user, the ultrasonic transducer determines a heart rate of the user.

In some embodiments, the visual stimulation generation component presents the targeted information responsive to assessing at least one of an amount of the at least one of the one or more items and an alternative item to the at least one of the one or more items based on at least one of a user profile, one or more learned characteristics of the user, one or more preferences indicated by the user, a day, and a time of day.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

Figure 1B:
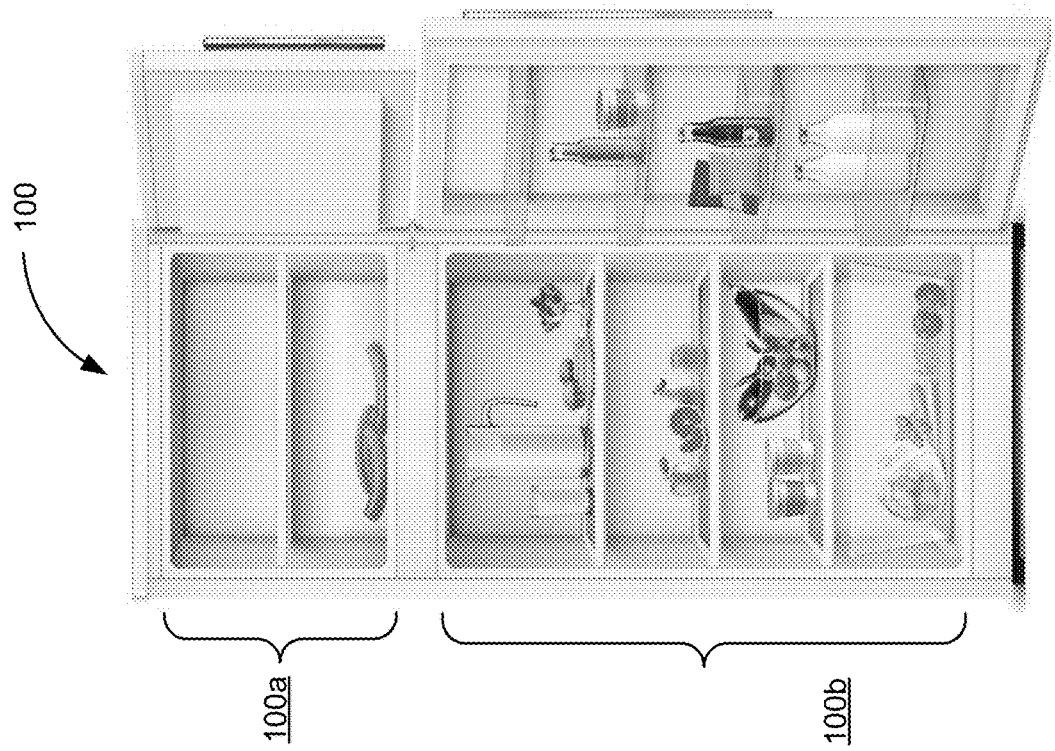
FIG. 1B illustrates a second view of the example EAS refrigerator of FIG. 1A

The figures are not exhaustive and do not limit the present disclosure to the precise form disclosed.

DETAILED DESCRIPTION

Various technologies exist and/or are being developed in the context of smart homes. For example, home appliances or components, such as light fixtures, multimedia systems, and the like, may be operatively connected to a home network, such as a home Wi-Fi network. In this way, a user may interact with such home appliances or components using the home network. For example, instead of a home occupant physically actuating a light switch, the home occupant may simply speak a command. One or more sensors/devices also connected to the home network may pick up on the home occupant's spoken command, and one or more signals or instructions may be sent to an applicable light fixture(s) or a light fixture(s) in some determined proximity to the home occupant's current location to activate (or deactivate) the light fixture(s).

Beyond such smart homes/smart technology, however, efforts are being made to realize affective computing, which can refer to the study and/or development of systems and devices that recognize, interpret, process, and simulate human affects (underlying experience of feeling, emotion, or mood). Accordingly, various embodiments are directed to an emotion-aware smart (EAS) refrigerator that can utilize contactless sensors to detect users, and read/monitor brainwave and/or heart rate activity of such users. Through affective computing, such an EAS refrigerator can understand a user's desires regarding the accessing of food (or other items) stored in the EAS refrigerator.

In particular, one or more sensors may detect the presence of a user proximate to the EAS refrigerator. Upon detecting the presence of the user, certain stimuli can be presented to the user to evoke an electrophysiological response from the user's nervous system including brainwave activity and/or heart rate/heart rate interval activity. In some embodiments, such an electrophysiological response can be a visual evoked potential (VEP). For example, the stimuli presented to the user can include visual stimuli, e.g., images or presentations of a EAS refrigerator's contents displayed at certain frequencies to the user. By detecting the user's brainwave activity in response to the visual stimuli (i.e., the user's VEP response), the user's interest in one or more of the refrigerator's contents can be gauged. It should be understood that some thresholds or other indicia of interest in using/accessing the EAS refrigerator may be used. For example, some amount of time that a user is sensed or detected being proximate to the EAS refrigerator, e.g., meeting/exceeding some determined threshold, can be measured to ascertain whether or not a user is actually interested in using/accessing the EAS refrigerator as opposed to merely walking by the EAS refrigerator. In some embodiments, direct-ness of a user's gaze/determining (or predicting) where a user is looking, etc. can be used an indicator of interest.

Beyond gauging a user's interest in the contents of an EAS refrigerator, the EAS refrigerator can also leverage the user's brainwave activity as well as heartrate response (obtained by electroencephalogram and electrocardiogram readings/measurements, respectively) to, e.g., determine a user's level of hunger. Based on this information or assessment, a desired item, along with an amount of that desired item can be recommended to the user. In other embodiments, certain user preferences or profiles or conditions may be taken into account when recommending an item of interest to the user. For example, if the user is not only hungry, but currently practicing a particular diet, the amount of a food item to be recommended to the user can be adjusted accordingly. Similarly, dietary restrictions can be taken into account. Alternatives to the item(s) of interest can be recommended to the user, and so on.

In still other embodiments, the user's VEP response can be considered along with other biometric information associated with the user. For example, a user may have other biometric indications, such as blood pressure levels (gleaned from blood pressure monitor), glucose levels (obtained from a glucose monitor), etc. These additional biometric indications may also be used to adapt or adjust recommendations by the EAS refrigerator. As another example, a smart weight scale may communicate with the EAS refrigerator so that a user's current weight may be considered along with the user's VEP response when recommending a food item and/or an amount of food.

Further still, in some embodiments, an EAS refrigerator can be used to detect the presence of potentially unwanted persons in a home. For example, the same sensors and/or mechanisms for detecting the presence of a user and/or detecting the VEP response of a user can be used to detect the presence of a person, not typically associated with the home in which the EAS refrigerator is installed or used (e.g., an intruder). In other embodiments, the same sensors and/or mechanisms for detecting the presence of a user and/or detecting the VEP response of a user can be used to detect if a person is having some form of medical emergency (e.g. heart attack or choking). It should be understood that the embodiments described herein are meant to be examples, and are not necessarily limiting.

Figure 1A:
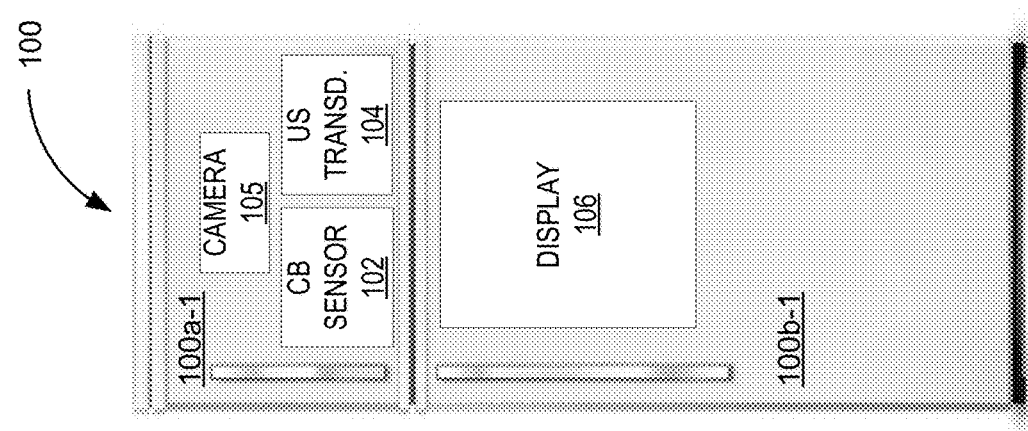
FIG. 1A illustrates a first view of an example emotion-aware smart (EAS) refrigerator in accordance with one embodiment.

FIG. 1A illustrates an example EAS refrigerator 100 in accordance with one embodiment of the present disclosure, and will be described in conjunction with FIG. 1B, which illustrates a second view of EAS refrigerator 100. As illustrated in FIG. 1B, EAS refrigerator 100 may have a freezer compartment 100a and a refrigeration compartment 100b. As illustrated in FIG. 1A, freezer compartment 100a may have a corresponding freezer compartment door 100a-1, and refrigeration compartment 100b may have a corresponding refrigeration compartment door 100b-1. As alluded to above, items to be maintained in a frozen state may be stored in freezer compartment 100a, while items to be maintained in a refrigerated state may be stored in refrigeration compartment 100b.

It should be understood that EAS refrigerator 100 is only one example of an EAS refrigerator. An EAS refrigerator may have various different configurations, e.g., different door configurations (side-by-side doors), bottom located freezer compartment, swing-out doors, slide-out doors, etc. An EAS refrigerator in accordance with other embodiments, may have only a refrigeration compartment. In some embodiments, an EAS device or appliance is contemplated, where only a freezer compartment is configured. An EAS refrigerator may be configured to have different internal organizational trays, cabinets, and so on. In other embodiments, an EAS refrigerator or appliance may have more types of compartments, e.g., one or more specialized refrigeration compartments and/or one or more specialized freezer compartments. A specialized compartment may maintain a particular refrigeration or frozen temperature/range of temperatures and can be used to store particular types of items. Although FIG. 1B only illustrates foodstuffs as being stored in EAS refrigerator 100, it should be understood that other non-food type items may be stored therein.

As further illustrated in FIG. 1A, EAS refrigerator may comprise at least one contactless brainwave (CB) sensor 102. One example of a CB sensor is referred to as a neurobiomonitoring sensor provided by Freer Logic. In some embodiments, CB sensor 102 may comprise a wireless electroencephalogram (EEG)-based sensor that can monitor/detect a person's brainwaves within some proximity threshold. As alluded to above, CB sensor 102 may detect a user's brainwave activity, e.g., a user's VEP response to stimuli presented on display 106 (described in greater detail below).

Additionally, EAS refrigerator 100 may include an additional sensor(s) such as a camera, e.g., camera 105, radar unit, an ultrasonic/ultrasound transducer or scanner 104, etc. Such additional sensor(s) can be used for user detection and/or identification. In the case of ultrasonic transducer 104, such a sensor may also be configured to monitor/detect a user's heart rate/heart rate activity. In some embodiments, ultrasonic transducer 104 may be configured to sense a user's hear rate/heart rate activity without a need for physical contact between the user and ultrasonic transducer 104.

In combination, and as will described in greater detail below, both a user's brainwave activity (gleaned from CB sensor 102) and the user's heart rate/heart rate activity (gleaned from ultrasonic transducer 104) can together indicate one or more aspects or characteristics of the user's hunger response. For example, and as alluded to above, from a user's brainwave activity and heart rate, the user's desire to consume a particular food item can be determined, as well as the amount of that food item that the user wants to consume. It should be understood that both heart rate and brainwave activity can be affected or impacted by a mental response to hunger or physiological hunger cues.

Moreover, due to the fusion of brainwave and heart rate activity monitoring/detection disclosed herein, other embodiments are contemplated. In one such other embodiment, the brainwave and heart rate activity of a particular user can be analyzed and used to create a profile, or otherwise used to identify that particular user. In this way, EAS refrigerator 100 can distinguish between a plurality of users, e.g., between family members, all or some of which use EAS refrigerator 100. As a result, the recommendations regarding the contents/amounts provided by EAS refrigerator 100 can be customized or targeted specifically to a user.

Additionally still, and as noted above, EAS refrigerator 100 may be used to identify an intruder. Because EAS refrigerator 100 can use the aforementioned combination of brainwave activity and heart rate/heart rate activity to identify particular users, if EAS refrigerator 100 senses a combination of brainwave activity and heart rate/heart rate activity that does not comport with or match a "profile" of a known user, EAS refrigerator may generate some indication (send an alert, text, call, otherwise transmit a notification) that an intruder or otherwise unrecognized person(s) has been sensed in its proximity. Moreover, other non-hunger/food related sensing or detection can be performed by EAS refrigerator 100. Emergencies such as personal injury (slip and fall, heart attack, etc.) may also be detected based on brainwave activity and heart rate activity. Accordingly, EAS refrigerator 100 can similarly transmit a notification(s) to a municipality, emergency agency, etc. informing that entity of an emergency situation that may necessitate an emergency response. EAS refrigerator 100 can also transmit such notifications to other users, e.g., parents, when an emergency situation is detected regarding a child.

Figure 2:
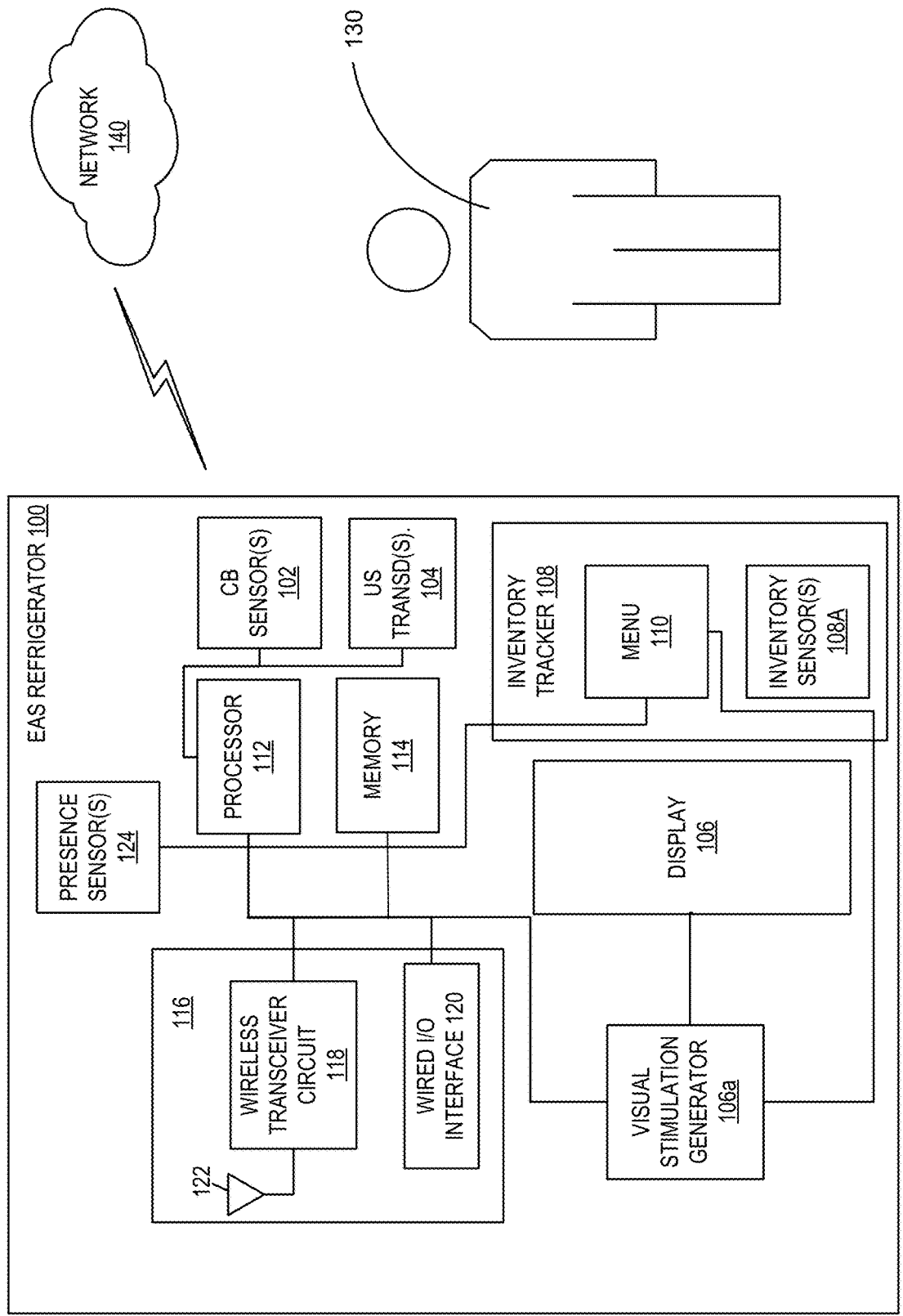
FIG. 2 illustrates components comprising and operating with the EAS refrigerator of FIGS. 1A and 1B.

FIG. 2 illustrates a schematic representation of various components of EAS refrigerator 100 in accordance with one embodiment. As already described above with respect to FIGS. 1A and 1B, EAS refrigerator 100 may comprise one or more CB sensors 102, an ultrasonic transducer 104, and a display 106. Additionally, EAS refrigerator 100 may comprise a processor 112, a memory 114, and a communication circuit 116, as well as a visual stimulation generator 106a, and an inventory tracker 108, that can comprise one or more inventory sensors 108A, which can generate a menu 110.

Processor 112 can include a GPU, CPU, microprocessor, or any other suitable processing system. The memory 114 may include one or more various forms of memory or data storage (e.g., flash, RAM, etc.) that may be used to store the calibration parameters, images (analysis or historic), point parameters, instructions and variables for processor 112 as well as any other suitable information. Memory 114 can be made up of one or more memory units of one or more different types of memory, and may be configured to store data and other information as well as operational instructions that may be used by the processor 112 to analyze information/signals/data obtained by CB sensor(s) 102 and ultrasonic transducer(s) 104.

Although the example of FIG. 2 is illustrated using processor and memory circuitry, as described below with reference to circuits disclosed herein, components such as communication circuit 116 can be implemented utilizing any form of circuitry including, for example, hardware, software, or a combination thereof. By way of further example, one or more processors, controllers, ASICs, PLAs, PALs, CPLDs, FPGAs, logical components, software routines or other mechanisms might be implemented to make up a driving mode circuit 210.

Communication circuit 116 may comprise either or both a wireless transceiver circuit 118 with an associated antenna 122 and a wired I/O interface 120 with an associated hardwired data port (not illustrated). As this example illustrates, communications with other components of EAS refrigerator 100 and/or network 140 can include either or both wired and wireless communications circuits 116. Wireless transceiver circuit 118 can include a transmitter and a receiver (not shown) to allow wireless communications via any of a number of communication protocols such as, for example, WiFi, Bluetooth, near field communications (NFC), Zigbee, and any of a number of other wireless communication protocols whether standardized, proprietary, open, point-to-point, networked or otherwise. Antenna 122 is coupled to wireless transceiver circuit 118 and is used by wireless transceiver circuit 118 to transmit radio signals wirelessly to wireless equipment with which it is connected and to receive radio signals as well. These RF signals can include information of almost any sort that is sent or received by communications circuit 116 to/from other entities such as CB sensor(s) 102, ultrasonic transducer 104, and so on. For example, network 140 may include a communications server/service (not shown) through which or to which the aforementioned notifications may be transmitted to a recipient.

Wired I/O interface 120 can include a transmitter and a receiver (not shown) for hardwired communications with other devices. For example, wired I/O interface 120 can provide a hardwired interface to other components, including CB sensor(s) 102, ultrasonic transducer 104, and so on. Wired I/O interface 120 can communicate with other devices using Ethernet or any of a number of other wired communication protocols whether standardized, proprietary, open, point-to-point, networked or otherwise.

A user 130, may be detected as being proximate to EAS refrigerator 100 vis-à-vis the existence of brainwave activity sensed by CB sensor(s) 102 and/or ultrasonic transducer 104. In other embodiments, sensors or devices, such as proximity sensors, cameras, heat sensors, and the like (illustrated as presence sensor(s) 124) may be used to detect the presence of a user proximate to EAS refrigerator 100. Upon sensing the presence of user 130, presence sensor(s) 124 may send a signal(s) to processor 112 indicating the presence of user 130/proximity of user 130 to EAS refrigerator 100. In turn, processor 112 may initiate an inventory assessment to be performed by inventory tracker 108. In some embodiments, processor 112 may simply instruct visual stimulation generator 106a to begin displaying images/icons (FIG. 3A) based on a current iteration/state of menu 110.

As noted above, display 106 may be used to present visual stimuli to a user. Display 106 may be any suitable type of display, e.g., a liquid crystal display (LCD), a light emitting diode (LED)-based display, etc. Display 106 may be a touch screen display in some embodiments. In some embodiments, and as illustrated in FIG. 1, display 106 may be implemented on an outer surface of EAS refrigerator 100, such as on one of doors 100a-1 or 100b-1. It should be understood that multiple displays can be provided with EAS refrigerator 100. For example, a household may have users of varying heights, and thus, those users of shorter stature, e.g., children, may be provided a display located on refrigeration compartment door 100b-1, while another display may be implemented on a surface of freezer compartment door 100a-1 to accommodate taller users. Although some embodiments implement display 106 on an outer surface of EAS refrigerator 100, display 106 (or multiple displays) may be implemented at an interior locations(s) of EAS refrigerator 100. In some embodiments, where multiple displays are provided, each may be driven by the same visual stimulation generator 106a, or may have their own respective visual stimuli generator components.

In operation, visual stimulation generator 106a may, based on menu 110 (which comprises a listing or other representation/information element(s) reflecting the items (or subset of items) being stored in EAS refrigerator 100), display one or more visual representations of the items. For example, visual stimulation generator 106a may comprise a repository of images, e.g., icons, that can correspond to various items that may be stored in a refrigerator, e.g., food items. Upon receiving an accounting of items stored in EAS refrigerator 100, visual stimulation generator may access its repository of images and present, for display on display 106, those icons or images corresponding to the items in menu 110. It should be noted that visual stimulation generator may comprise any known or future-developed graphical/image processing unit capable of presenting images on a display. As will be discussed below, these images may be displayed to a user such that the images oscillate at particular frequencies.

Inventory tracker 108 may comprise a component or logic executed by processor 112 for assessing the inventory of item(s) currently present in EAS refrigerator 100. For example, EAS refrigerator 100 may further include one or more inventory sensor(s) 108a that are capable of tracking those item(s) currently stored/kept in EAS refrigerator 100. Inventory sensor(s) 108a can be pressure sensors, one or more cameras, or other known sensors that may be appropriately used to track items in EAS refrigerator 100. For example, and referring back to FIG. 1B, pressure sensors may be located on surfaces atop which items may be placed. In some embodiments, certain section of refrigeration compartment 100b and freezer compartment 100a may be specified for certain items or types of items. In this way, the presence of an item(s) on one or more of inventory sensor(s) 108a can be registered/detected. Such information can be used by inventory tracker 108 to generate menu 110 indicative of a current inventory of items in EAS refrigerator 100.

It should be understood that inventory tracker 108 may continuously query inventory sensor(s) 108a to maintain a current and up-to-date inventory of items reflected by menu 110. In some embodiments, inventory tracker 108 may be configured to track respective amounts of items stored in EAS refrigerator 100. In other embodiments, processor 112 may only prompt inventory tracker 108 to take inventory of EAS refrigerator 100 upon sensing the presence of a user, e.g., user 130. Upon sensing user 130, processor 112 may instruct inventory tracker 108 to query inventory sensor(s) 108a to assess the current item(s) and/or amounts of such item(s) in EAS refrigerator 100. Menu 110 may then be generated or updated to reflect this current inventory.

It should be further noted that inventory tracker 108 may be further configured to electronically re-order/send a purchase request for items upon a determination that a particular item has been depleted or falls below some defined threshold amount. For example, upon assessing a current inventory of items in EAS refrigerator 100, inventory 108 may compare the items making up menu 110 to a list/listing of items specified as items to be automatically re-ordered for replenishment. Accordingly, EAS refrigerator 100 may communicate with/through network 140 to, e.g., an online ordering portal, website, marketplace, etc., to place an order to replenish those items.

Figure 3A:
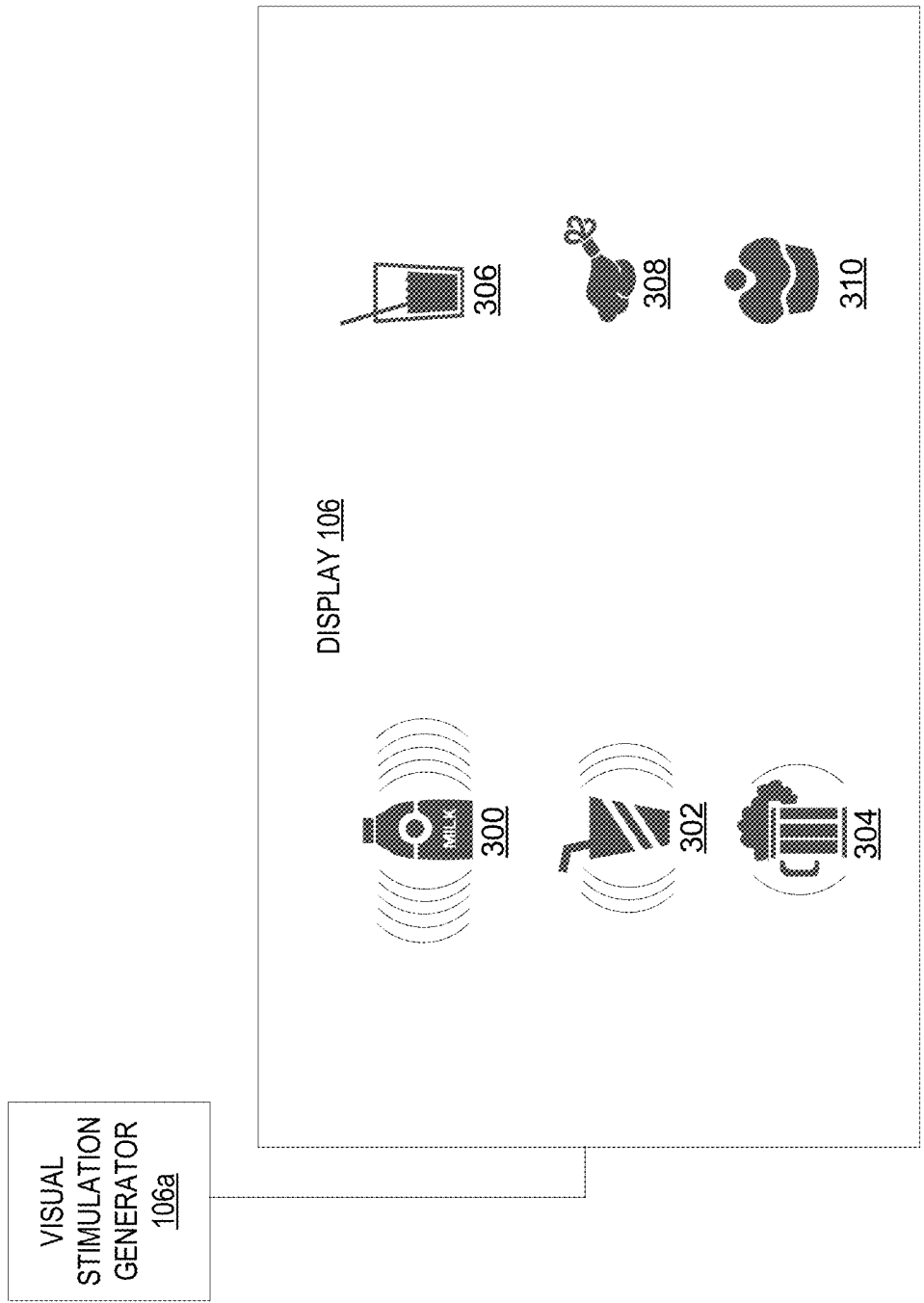
FIG. 3A illustrates an example of visual stimuli that can be presented by the example EAS refrigerator of FIGS. 1A and 1B.

Referring to FIG. 3A, visual stimulation generator 106a may, based on the contents of/items stored in EAS refrigerator 100 reflected in menu 110, present images representative of those items on display 106. As illustrated in FIG. 3A, and for example, visual stimulation generator 106a may present images or icons representative of the following: a milk carton 300; a glass of soda 302; a mug of beer 304; an apple 306; a chicken leg 308, and/or a cupcake 310. As illustrated in FIG. 3A, these images or icons may be presented in such a way that each or some of the images/icons oscillate or appear to vibrate in accordance with a particular frequency, each different from the other.

It should be understood that in some embodiments, the images or icons presented by visual stimulation generator 106a may be representative of particular items contained in EAS refrigerator 100. For example, if menu 110 indicates that a chicken leg is present in EAS refrigerator 100, visual stimulation generator 106a will present an icon of that chicken leg, e.g., chicken leg 308. In other embodiments, visual stimulation generator 106a may present icons or images that represent a particular type or class of food. For example, when presenting an icon representative of milk carton 300 on display 106, milk carton 300 may be representative of any/all dairy items in EAS refrigerator 100. Thus, it should be understood that visual stimulation generator 106a can be configured or instructed to present images/icons in accordance with one or more desired schema. For example, a user may desire a more general representation of food items to be presented, while another user may desire a more refined/granular representation of food items. In some embodiments EAS refrigerator 100 may be programmed during/after manufacture to display images/icons in a desired manner. In some embodiments a user may, at his/her discretion, specify how items are to be display/in accordance with a desired schema. That is, a user may input his/her preferences to EAS refrigerator 100/visual stimulation generator 106a through known input mechanisms. For example, and as alluded to above, display 106 may be a touchscreen display, and a user may (in a menu screen, not shown) specify how he/she would like the contents of EAS refrigerator 106a to be presented, e.g., whether indicative of particular food items, a particular type of food item, some combination thereof, and so on. In some embodiments, EAS refrigerator 100 may have other input mechanisms, e.g., microphones, physical or soft buttons, etc. through which these preferences may be input.

In some embodiments, the same/similar input mechanisms can be used by a user to define food or stored item categories, classes, etc. This may be accomplished by providing such input to inventory tracer 108 to customize menu 110, for example. For example, a user may wish to see items displayed in accordance with whether or not they comport with a particular diet plan being followed by the user. It should be understood that the preceding examples are just examples, and not intended to be limiting.

When visual stimulation generator 106a presents one or images oscillating at differing frequencies (as illustrated in FIG. 3A), CB sensor(s) 102 are capable of assessing, via the brainwaves captured by CB sensor(s) 102, which item(s) being presented are being focused on by a user. That is, an assumption can be made that if a user responds to a particular displayed oscillation frequency, the user is interested in that displayed item/class of items. That is, when a user is exposed to certain visual stimuli oscillating at a particular frequency, e.g., 10 Hz, the visual cortex of the user's brain may recognize and register that oscillatory behavior. As such, recording electroencephalogram data from the visual cortex allows for the extraction of that oscillatory behavior to indicate which visual stimuli a user reacts to/focuses on (similar to extracting EEG/EKG data).

As illustrated in FIG. 3A, images or icons may be presented simultaneously to a user, e.g., user 130 (FIG. 2). However, it should be understood that such images/icons may be presented, e.g., one at a time, or in defined subsets. Accordingly, a user's VEP response can be gauged depending on brainwave activity received by CB sensor(s) 102 commensurate with the item being displayed on display 106. That is, visual stimulation generator 106a may cycle through images/icons and present each item (or some grouping thereof) on display 106. A user's brainwave activity may be registered as being more active or less active in accordance with different items being presented. In other words, in some embodiments, visual stimulation generator 106a need not necessarily (although it may) present images/icons in a non-oscillating fashion, and CB sensor(s) 102 may still be able to identify, through brainwave activity associated with images presented on display 106. For example, different colors may be assigned to certain items such that images/icons presented to a user may be displayed with/in a certain color, encoded with a particular color for display, etc. In some embodiments, a combination of triggers, e.g., color and oscillation frequency, may be used to elicit a VEP response.

It should be understood that ultrasonic transducer(s) 104 may, similar to CB sensor(s) 102, sense activity of user 130, except instead of brainwave activity, heart rate or heart rate activity. For example, upon seeing milk carton 300 presented on display 106 at a particular frequency (or in response to the presentation of milk carton 300 alone on display 106), user 130's VEP response suggest interest in milk (or related diary product). The user 130's heart rate may also rise or spike, which can be interpreted as a sign that user 130 is expressing a strong level of interest in/a desire to consume milk (or a related dairy product). That is, in some embodiments, the VEP response can be used to ascertain user interest in a particular item, while heart rate/heart rate activity can be used to gauge the user's level of interest in that particular item. It should be understood that detecting and interpreting interest in/user 130's response to a particular displayed item(s) can be effectuated in various ways.

Processor 112 may analyze the brainwave activity and heart rate/heart rate activity sensed by CB sensor(s) 102 and ultrasonic transducer(s) 104 to determine the aforementioned interest/disinterest and level of interest. For example, memory 114 may contain code or specified logic/algorithm(s) that can assess interest/disinterest based on the received signals from CB sensor(s) 102. Level of interest can be determined based on signals from ultrasonic transducer(s) 104. For example, processor 112 may, upon receipt of such signals, compare the signals to some specified threshold(s). Based on how close to, how far from, how much such specified threshold(s) are surpassed, etc., processor 112 can make a determination as to level of interest regarding a particular item(s) presented to user 130.

Figure 3B:
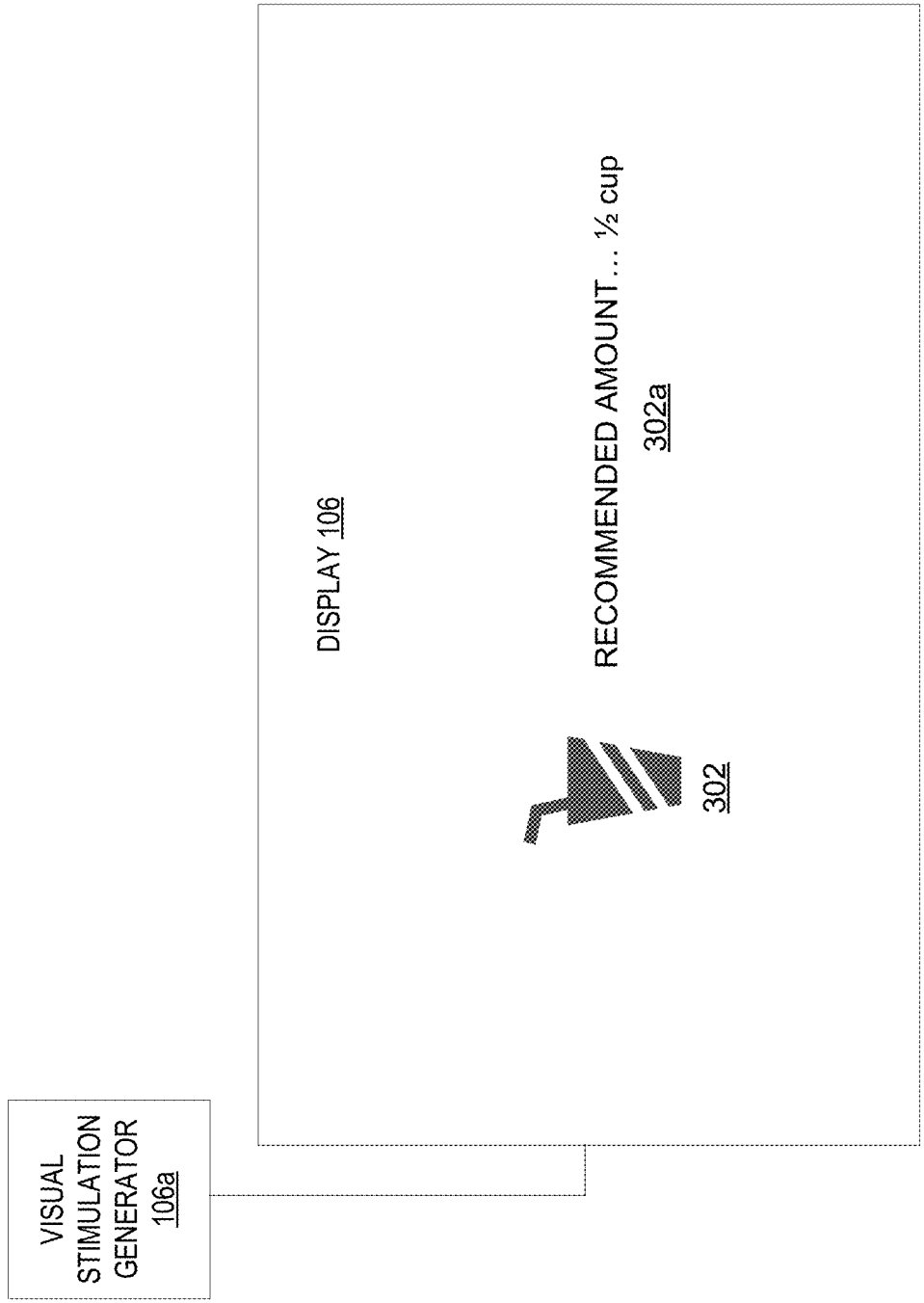
FIG. 3B illustrates an example of targeted information regarding an item of interest that can be presented by the example EAS refrigerator of FIGS. 1A and 1B.

Processor 112 may then relay this interest/disinterest information or data to visual stimulation generator 106a which may then display the item of interest along with a recommended amount or other information associated with the user/consumption of that item. For example, as illustrated in FIG. 3B, upon a determination that user 130, via brainwave activity is interested in soda, image 302 may be presented on display 106 to user 130 along with information, such as a recommended amount of soda 302a, based on heart rate/heart rate activity information. That is, EAS refrigerator 100 can adapt offerings of items to user 130 based on one or more criteria. As noted above, a profile of user 130 may be considered when presenting such adaptations to the user 130. For example, the profile may indicate food preferences, preferred amounts of food, dietary constraints, dietary goals, etc. associated with user 130. Accordingly, such information can be presented based on one or more aspects of this profile. If no profile exists, or if a particular item/type of item is not specified in a profile, a default amount may be recommended to user 130. In other embodiments, a new profile can be created. As a start/default, a user may manually specify/determine desired/recommended food quantities, dietary choices, etc. In some embodiments, and over time, information or data regarding a user's interest/disinterest in an item, along with level of interest (or disinterest) can be collected and used to, e.g., update a user's profile.

In other embodiments, processor 112 may consider a profile of user 130 (stored in memory 114), by comparing determined interest/disinterest in a particular item(s) with the profile. If the profile indicates that user 130 is following/should be following some diet that includes some dietary restrictions, processor 112 may present another item(s) different from that determined to be of interest to user 130. For example, instead of presenting a recommended amount of soda (FIG. 3B) to user 130, processor 112 may instruct visual stimulation generator 106a to present an alternative item(s) to user 130 that better comports with such dietary restrictions, e.g., an image of juice 306 (FIG. 3A). In other embodiments, recommended amounts of an item can be adjusted and presented to user 130 depending on such considerations. It should be noted that a profile is not necessarily required in other embodiments. For example, upon determining a menu 110 of items currently stored in EAS refrigerator 100, user 130 may input one or more parameters or information/data akin to a profile(s). For example, user 130 may be interested in consuming some food item with a high amount of protein after a workout. Accordingly, user 130 may specify he/she has had a workout, and in response, processor 112 may (using logic/algorithm(s) stored in memory 114), compare food items that fall into a protein-heavy category, and determine if a current menu 110 includes any item(s) that match or fall into the protein-heavy category. If so, processor 112 may instruct visual stimulation generator 106a to display such food items to user 130 via display 106. If no match is found, processor 112 may present a determined alternative to user 130 or may present an indication via display 106 that nothing matching the desire/requirements set forth by user 130 are present in EAS refrigerator 100. In some embodiments, such an indication may trigger re-ordering or ordering of one or more items that would satisfy the specified desires/needs/requirements of user 130. It should be understood that many other scenarios and/or considerations known or understood by those of ordinary skill in the art may be taken into account in accordance with other embodiments. That is, the above-mentioned logic/algorithms may comport with dietician-specified programs, user-specified programs, and so on.

It should be understood that the aforementioned determination logic/algorithms and/or the aforementioned user profiles can be determined, generated and/or adapted based on machine learning or artificial intelligence mechanisms. Machine learning generally involves developing a model, i.e., a mathematical representation of a real-world process, where the model is able to make predictions about that real-world process. To generate a model, typically, training data is provided or input into a machine learning algorithm by means of a known dataset before application of the model in real-world scenarios or situations. Accordingly, EAS refrigerator 100 may, via memory 114 and processor 112 and/or inventory tracker 108, utilize machine learning techniques to customize interest/disinterest determinations, adapted presentations of recommended items, etc. to user 130. Ultimately, over time/some learning period, the model should be able to accurately predict/estimate what user 130 desires to consume, what item(s) to display based on sensed brainwave/heart rate activity, etc. In this way, EAS refrigerator 100 may learn to better assess user 130's wants/needs and/or what to present to user 130. In some embodiments, such machine learning techniques may be applied to visual stimulation generator 106a to direct visual stimulation generator 106a to display or present items in accordance with a specific order meant to comport with a profile, specified needs/goals of a user, etc.

Figure 4:
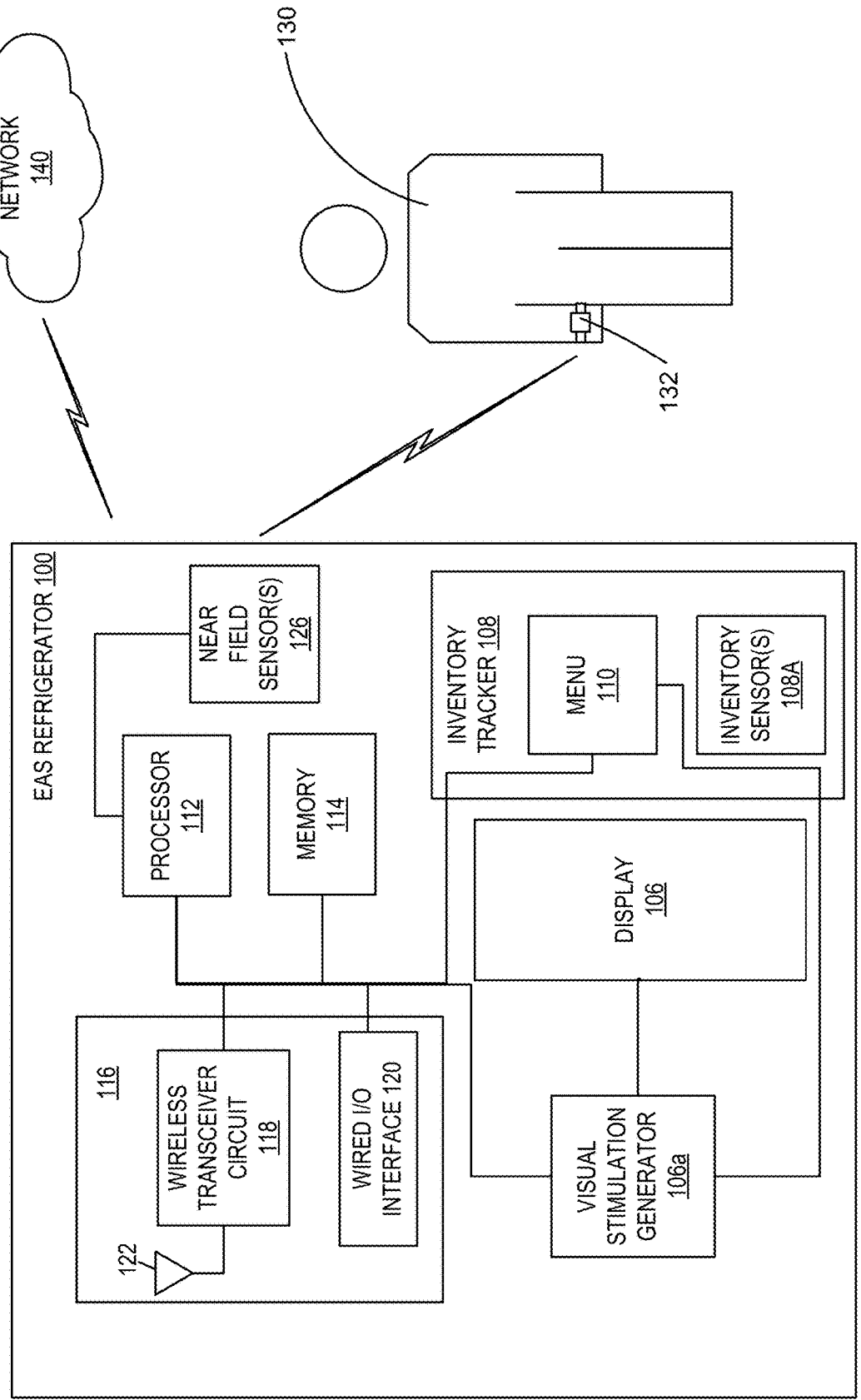
FIG. 4 illustrates components comprising and operating with an EAS refrigerator in accordance with another embodiment.

FIG. 4 illustrates another embodiment of the disclosed technology, whereby as an alternative to the use of CB sensor(s) 102 and/or ultrasonic transducer(s) 104, user 130 may employ a wearable sensor(s) 132 configured to capture similar brainwave and/or heart rate activity information. It should be noted that one or both of CB sensor(s) 102 and/or ultrasonic transducer(s) 104 may be replaced with wearable sensor(s) 132. Moreover, it should be noted that although wearable sensor(s) 132 is illustrated in FIG. 4 as having a watch or watch-like form factor, wearable sensor(s) 132 may comprise wearable sensors in the form of eyewear, headwear, clothing, and so on. Information regarding the brainwave and/or heart rate activity sensed by wearable sensor(s) 132 may be relayed to EAS refrigerator 100 vis-à-vis a near field sensor(s) 126 or similar sensor/receiver. Upon receipt of such information, the elements common between FIGS. 2 and 4 may perform/act similarly to ascertain user 130's interest/disinterest in one or more items, present items, amounts of items, and so on to user 130.

Figure 5:
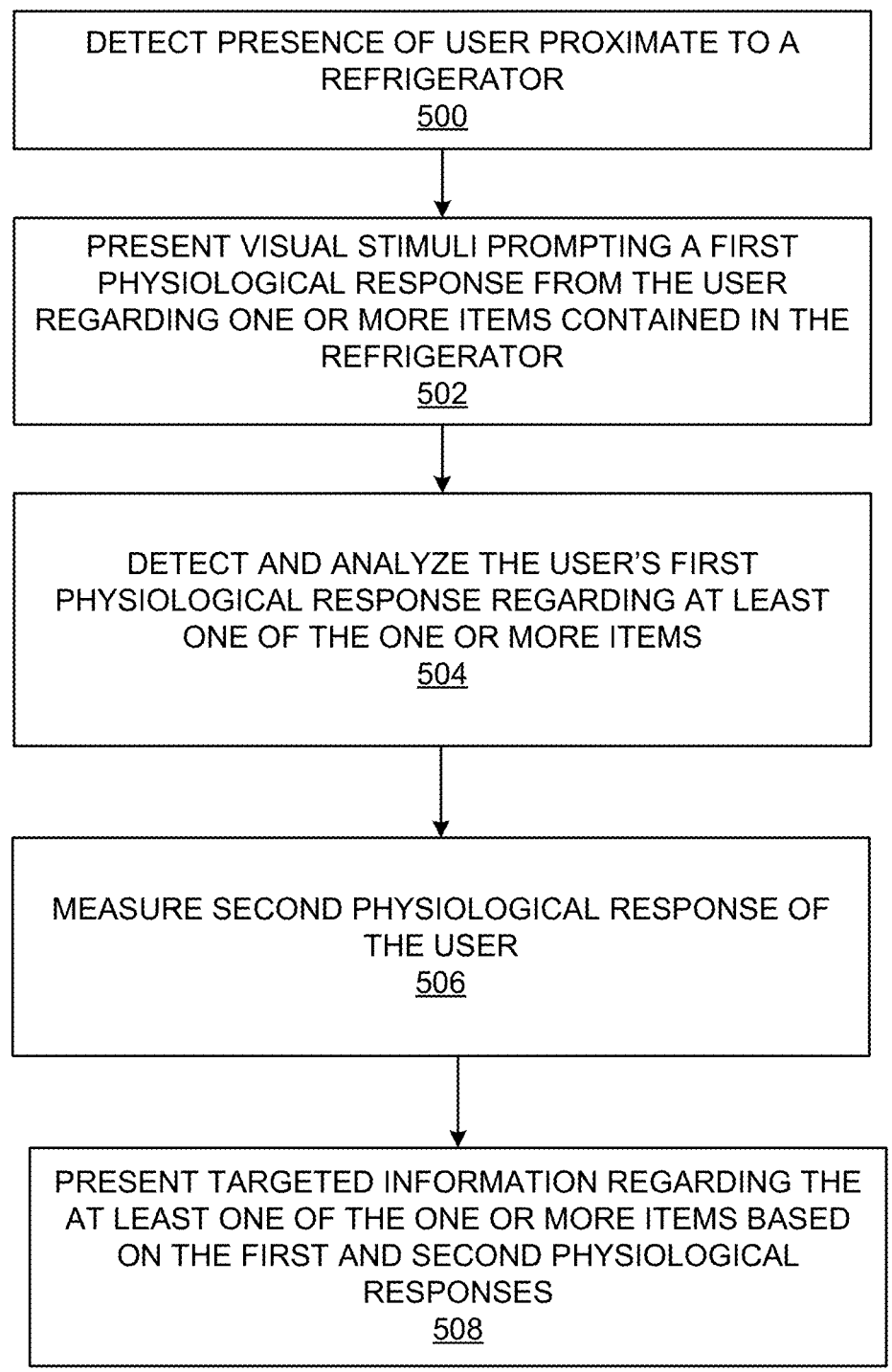
FIG. 5 is a flow chart illustrating refrigerator-based affective computing in accordance with one embodiment.

FIG. 5 is a flow chart illustrating example operations that may be performed to effectuate affective computing using contactless sensors an EAS refrigerator. At operation 500, the presence of a user proximate to a refrigerator, such as an EAS refrigerator can be detected. As described above, one or more sensors, such as presence sensors (cameras, proximity, etc.) may be used to detect the presence of a user proximate to the refrigerator. It should be noted that various mechanisms may be used to gauge proximity. For example, any person passing by the refrigerator can potentially be sensed by a presence sensor. However, in some embodiments, measurements may be taken based on the sensed presence information to determine proximity as an indicator that a sensed person is actually interested in engaging with the EAS refrigerator. For example, if a camera senses the presence of a user, the camera may compare the size of the sensed user's head/facial features to thresholds to determine whether or not the user is close enough to suggest he/she wishes to engage with the EAS refrigerator. For example, memory 114 of EAS refrigerator 100 may include one or more measurements that if met within some range, can be interpreted to mean the user is close enough to warrant initiation of visual stimulation presentations of items. If the one or more measurements do not fall with the specified range, processor 112 may be configured to determine that the user is too far to warrant engagement therewith. Other mechanisms for determining proximity or the threshold amount of proximity to begin operation of EAS refrigerator regarding contactless brainwave monitoring may be used. It should be understood that in other embodiments, proximity may not be taken into account. Rather, the mere sensing of a user may prompt EAS refrigerator to begin presenting visual stimuli. However, if no VEP response is received/sensed (or if no continued VEP response is received/sensed) EAS refrigerator may return to a waiting or idle state. If, however, a threshold amount or continued duration of VEP response is sensed, EAS refrigerator may continue its operation.

At operation 502, visual stimuli prompting a first physiological response, e.g., VEP response, from the user regarding one or more items contained in the refrigerator may be presented. As previously described, a visual stimulation generator, such as visual stimulation generator 106a may, depending on menu 110 (and potentially, in accordance with other considerations such as user profile, receipt of relevant parameters, and so on), present one or more images representative of such items to the user. In some embodiments, the images are presented in an oscillating fashion at particular frequencies, etc. The manner in which such images can be presented are intended to evoke a VEP response from the user which can clue EAS refrigerator in to potential interest in one or more items.

Thus, at operation 504, the user's first physiological response can be detected and analyzed regarding at least one of the one or more items. Detection of the user's first physiological/VEP response can be accomplished using one or more CB sensors implemented in/on the refrigerator. Analysis of the user's VEP response may involve determining a correlation between the user's sensed brainwave activity to the frequency at which a presented image (representing an item) oscillates. In some embodiments, analysis of the user's VEP response may correlate a level of the user's brainwave activity to a particular item. Other methods or mechanisms for gauging the user's interest in one or more of the presented items based on the user's VEP response can be used.

At operation 506, a second physiological response of the user can be measured. As described above, such physiological responses can include heart rate or heart rate activity, that in some embodiments can be sensed by an ultrasonic transducer. It should be understood that other types of sensors may be utilized to gauge other/additional physiological responses by the user. For example, the presence sensor(s), e.g., camera, may be used to gauge facial expressions of the user, eye movement(s) body movement(s)/language exhibited by the user, etc. It should be understood that those of ordinary skill in the art are aware of other user responses that may indicate some interest or other characteristic relative to one or more items, and sensing/analyzing such responses can be implemented in these or other contemplated embodiments.

At operation 508, targeted information regarding the at least one of the one or more items can be presented based on the first and second physiological responses. That is, and described above, the user's VEP response in conjunction with, e.g., heart rate/heart rate activity information can be used to present targeted information about an item(s) of interest to the user. For example, in some embodiments, a recommended amount of an item determined to be desired by the user can be presented based on an assessment of the user's level of hunger (based on one or more of the user's first and second physiological responses). For example, high heart rate activity may indicate the user was previously engaged in high levels of physical activity suggesting he/she is hungry for a larger (than normal) amount of the desired item. In some embodiments, the physiological response can "directly" suggest some amount of an item to be presented to the user. As noted above, a user profile can be developed, and/or machine learning or artificial intelligence mechanisms can be used to learn a user's desired regarding items stored in the refrigerator. For example, over time, the refrigerator may learn that at a particular time of day, the user works out. Accordingly, upon sensing the user as being proximate to the refrigerator within some specified time period or specified day, and after that time of day/on that day (when the user typically works out), a machine learning model may predict that the user wishes to consume a particular amount of protein. Accordingly, depending on the item(s) in which the user evidences interest (e.g., vis-à-vis his/her VEP response), the refrigerator review the items of interest and select one associated with/known as having a high protein content, and/or suggesting an amount of that item for the user to consume. Again, such examples are non-limiting, and those of ordinary skill in the art would understand various factors/considerations that may be used as a basis for presenting the targeted information, and how to effectuate logic, circuitry, etc. to allow for such factors/considerations to be taken into account, as well as resulting targeted information.

Figure 6:
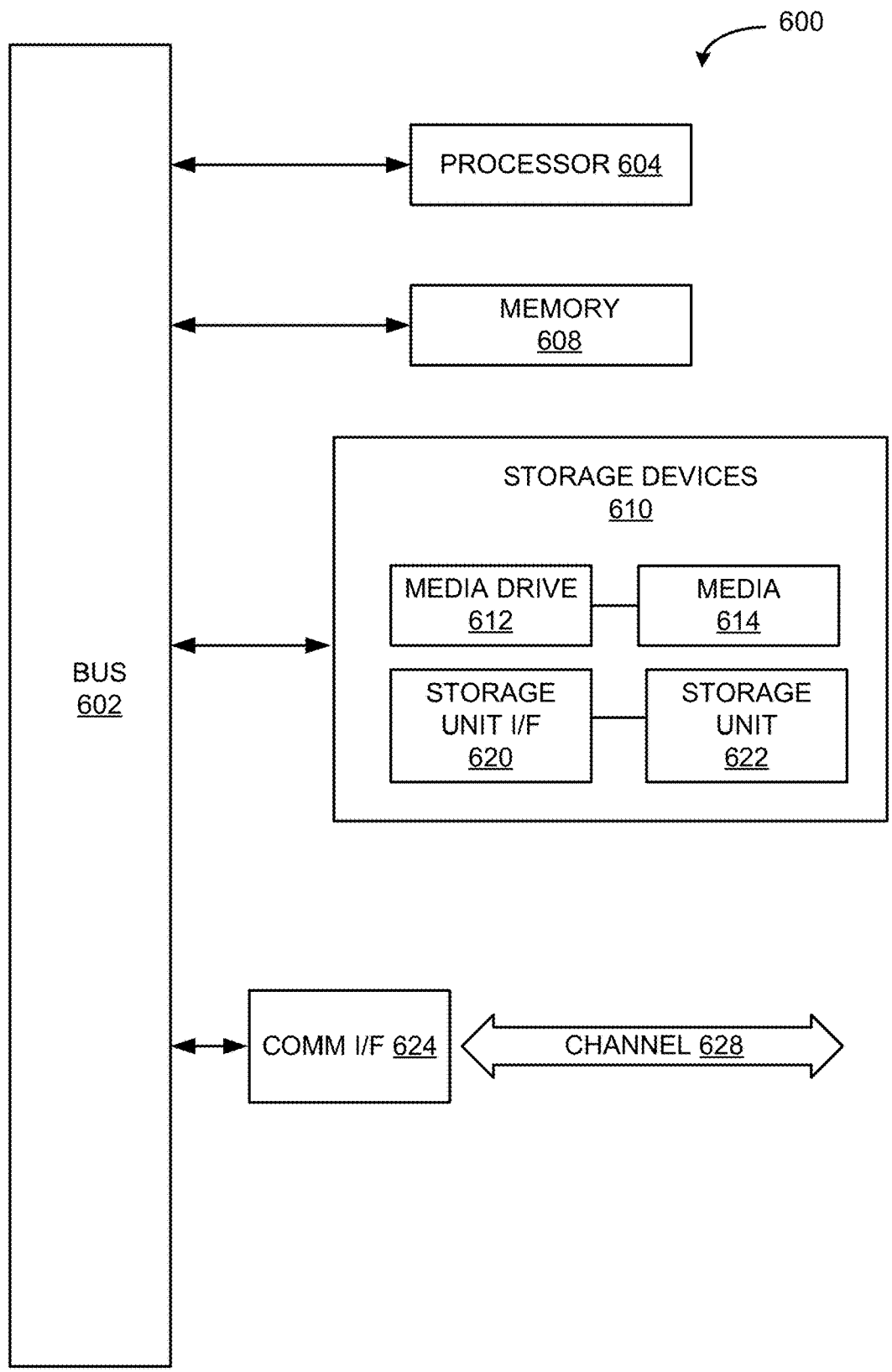
FIG. 6 is an example computing component that may be used to implement various features of embodiments described in the present disclosure.

As used herein, the terms circuit and component might describe a given unit of functionality that can be performed in accordance with one or more embodiments of the present application. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 6. Various embodiments are described in terms of this example-computing component 600. After reading this description, it will become apparent to a person skilled in the relevant art how to implement the application using other computing components or architectures.

Referring now to FIG. 6, computing component 600 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 600 might also represent computing capabilities embedded within or otherwise available to a given device. For example, a computing component might be found in other electronic devices such as, for example, portable computing devices, and other electronic devices that might include some form of processing capability.

Computing component 600 might include, for example, one or more processors, controllers, control components, or other processing devices. This can include a processor 604. Processor 604 might be implemented using a general-purpose or special-purpose processing engine such as, for example, a microprocessor, controller, or other control logic. Processor 604 may be connected to a bus 602. However, any communication medium can be used to facilitate interaction with other components of computing component 600 or to communicate externally.

Computing component 600 might also include one or more memory components, simply referred to herein as main memory 608. For example, random access memory (RAM) or other dynamic memory, might be used for storing information and instructions to be executed by processor 604. Main memory 608 might also be used for storing temporary variables or other intermediate information during execution of instructions to be executed by processor 604. Computing component 600 might likewise include a read only memory ("ROM") or other static storage device coupled to bus 602 for storing static information and instructions for processor 604.

The computing component 600 might also include one or more various forms of information storage mechanism 610, which might include, for example, a media drive 612 and a storage unit interface 620. The media drive 612 might include a drive or other mechanism to support fixed or removable storage media 614. For example, a hard disk drive, a solid-state drive, a magnetic tape drive, an optical drive, a compact disc (CD) or digital video disc (DVD) drive (R or RW), or other removable or fixed media drive might be provided. Storage media 614 might include, for example, a hard disk, an integrated circuit assembly, magnetic tape, cartridge, optical disk, a CD or DVD. Storage media 614 may be any other fixed or removable medium that is read by, written to or accessed by media drive 612. As these examples illustrate, the storage media 614 can include a computer usable storage medium having stored therein computer software or data.

In alternative embodiments, information storage mechanism 610 might include other similar instrumentalities for allowing computer programs or other instructions or data to be loaded into computing component 600. Such instrumentalities might include, for example, a fixed or removable storage unit 622 and an interface 620. Examples of such storage units 622 and interfaces 620 can include a program cartridge and cartridge interface, a removable memory (for example, a flash memory or other removable memory component) and memory slot. Other examples may include a PCMCIA slot and card, and other fixed or removable storage units 622 and interfaces 620 that allow software and data to be transferred from storage unit 622 to computing component 600.

Computing component 600 might also include a communications interface 624. Communications interface 624 might be used to allow software and data to be transferred between computing component 600 and external devices. Examples of communications interface 624 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 624 may be carried on signals, which can be electronic, electromagnetic (which includes optical) or other signals capable of being exchanged by a given communications interface 624. These signals might be provided to communications interface 624 via a channel 628. Channel 628 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 608, storage unit 620, media 614, and channel 628. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 600 to perform features or functions of the present application as discussed herein.

It should be understood that the various features, aspects and functionality described in one or more of the individual embodiments are not limited in their applicability to the particular embodiment with which they are described. Instead, they can be applied, alone or in various combinations, to one or more other embodiments, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method, comprising:
    detecting presence of a user proximate to a refrigerator;
    presenting one or more items contained in the refrigerator as visual stimuli displayed on a display of the refrigerator, the visual stimuli prompting a first physiological response from the user regarding the one or more items;
    detecting and analyzing the user's first physiological response to the visual stimuli, wherein detecting the user's first physiological response comprises sensing the user's brainwave activity via at least one contactless brainwave sensor configured to wirelessly monitor the user's brainwave activity, and wherein the first physiological response comprises a visual evoked potential (VEP) response;

selecting an item of the one or more items based on analyzing the first physiological response to the visual stimuli;

measuring a second physiological response of the user to the visual stimuli via an ultrasonic transducer or a camera;

determining a level of interest of the user in the selected item based on the second physiological response; and presenting, via the display of the refrigerator, targeted information regarding the selected one or more items based on the determined level of interest.

2. The method of claim 1, wherein presenting the visual stimuli comprises presenting one or more images representative of the one or more items to the user on the display, and wherein the presented one or more images oscillate at unique frequencies.

3. The method of claim 1, wherein presenting the visual stimuli comprises presenting one or more images representative of the one or more items to the user on the display in accordance with a particular order.

4. The method of claim 1, wherein the one or more items correspond to a current inventory of items contained in the refrigerator.

5. The method of claim 1, wherein analyzing the user's VEP response comprises correlating the user's brainwave activity to identify the selected item of the one or more items as indicative of an item of interest to the user.

6. The method of claim 1, wherein measuring the second physiological response of the user comprises determining heart rate activity of the user.

7. The method of claim 6, wherein determining a level of interest of the user in the selected item based on the measured second physiological response comprises:

comparing the determined heart rate activity to a threshold; and determining the level of interest of the user based on a difference between the determined heart rate activity and the threshold, wherein a larger difference between the determined heart rate activity and the threshold corresponds to a greater level of interest.

8. The method of claim 1, wherein measuring the second physiological response of the user comprises determining at least one of body movements and facial expressions.

9. The method of claim 1, wherein presenting the targeted information comprises presenting a recommended amount of the selected item of one or more items to the user.

10. The method of claim 9, wherein the recommended amount of the selected item is based on the determined level of interest.

11. The method of claim 1, wherein presenting the targeted information comprises assessing at least one of an amount of the selected item of the one or more items and an alternative item to the selected item of the one or more items based on at least one of a user profile, one or more learned characteristics of the user, one or more preferences indicated by the user, a day, and a time of day.

12. A refrigerator, comprising:

a presence sensor detecting presence of a user proximate to the refrigerator;

a visual stimulation generation component to present one or more items contained in the refrigerator as visual stimuli on a display of the refrigerator prompting a visual evoked potential (VEP) response from the user regarding one or more items contained in the refrigerator;

a contactless brainwave sensor to detect the user's VEP response to the visual stimuli;

a processor to analyze the user's VEP response to the visual stimuli and select an item of the one or more items based on analyzing the user's VEP response; and an ultrasonic transducer to measure an interest level response of the user;

wherein the processor further determines a level of interest of the user in the selected item based on the interest level response of the user, and wherein the visual stimulation generation component further presents targeted information regarding the selected item of the one or more items based on the determined level of interest.

13. The refrigerator of claim 12, wherein the visual stimulation generation component presents the visual stimuli by presenting one or more images representative of the one or more items to the user on the display, and wherein the presented one or more images oscillate at unique frequencies.

14. The refrigerator of claim 12, further comprising an inventory tracking component tracking and maintaining a current inventory of items contained in the refrigerator.

15. The refrigerator of claim 12, further comprising a processor to correlate the user's brainwave activity evidenced by the user's VEP response to identify the selected item of the one or more items as indicative of an item of interest to the user.

16. The refrigerator of claim 12, wherein to measure the interest level response of the user, the ultrasonic transducer determines a heart rate of the user.

17. The refrigerator of claim 16, wherein determining a level of interest of the user in the selected item based on the measured interest level response comprises:

comparing the determined heart rate activity to a threshold; and determining the level of interest of the user based on a difference between the determined heart rate activity and the threshold, wherein a larger difference between the determined heart rate activity and the threshold corresponds to a greater level of interest.

18. The refrigerator of claim 16, wherein presenting the targeted information comprises presenting a recommended amount of the selected item of one or more items to the user.

19. The refrigerator of claim 18, wherein the recommended amount of the selected item is based on the determined level of interest.

20. The refrigerator of claim 12, wherein the visual stimulation generation component presents the targeted information responsive to assessing at least one of an amount of the selected item of the one or more items and an alternative item to the selected item of the one or more items based on at least one of a user profile, one or more learned characteristics of the user, one or more preferences indicated by the user, a day, and a time of day.

* * * * *